(12) United States Patent
Beck et al.

(10) Patent No.: US 9,383,316 B2
(45) Date of Patent: Jul. 5, 2016

(54) METHOD OF MEASURING VAPOR FLUX DENSITY

(71) Applicant: First Solar, Inc., Perrysburg, OH (US)

(72) Inventors: Markus E. Beck, Scotts Valley, CA (US); Ulrich A. Bonne, Sunnyvale, CA (US); Raffi Garabedian, Los Altos, CA (US); Erel Milshtein, Cupertino, CA (US); Ming Lun Yu, Fremont, CA (US)

(73) Assignee: First Solar, Inc., Perrysburg, OH (US)

( * ) Notice: Subject to any disclaimer, the term of this patent is extended or adjusted under 35 U.S.C. 154(b) by 204 days.

(21) Appl. No.: 14/140,687

(22) Filed: Dec. 26, 2013

(65) Prior Publication Data

US 2014/0104616 A1 Apr. 17, 2014

Related U.S. Application Data

(62) Division of application No. 12/981,759, filed on Dec. 30, 2010, now Pat. No. 8,646,408.

(60) Provisional application No. 61/291,752, filed on Dec. 31, 2009.

(51) Int. Cl.
  *C23C 14/54* (2006.01)
  *C23C 16/52* (2006.01)
  *G01N 21/59* (2006.01)
  *G01N 21/31* (2006.01)
  *G01N 21/39* (2006.01)

(52) U.S. Cl.
  CPC .......... *G01N 21/5907* (2013.01); *C23C 14/544* (2013.01); *G01N 21/3103* (2013.01); *G01N 21/39* (2013.01); *G01N 2021/399* (2013.01)

(58) Field of Classification Search
  CPC .............................. C23C 16/52; C23C 14/544
  See application file for complete search history.

(56) References Cited

U.S. PATENT DOCUMENTS

| | | | |
|---|---|---|---|
| 3,612,859 A | 10/1971 | Schumacher | |
| 4,036,167 A | 7/1977 | Lu | |
| 4,377,238 A | 3/1983 | Wilks et al. | |
| 5,598,260 A | 1/1997 | Brewer et al. | |
| 5,880,823 A * | 3/1999 | Lu | G01J 3/42 118/712 |
| 6,038,017 A | 3/2000 | Pinsukanjana et al. | |
| 6,040,914 A | 3/2000 | Bortz et al. | |
| 6,075,588 A | 6/2000 | Pinsukanjana et al. | |
| 6,391,647 B1 | 5/2002 | Sperling et al. | |
| 6,891,612 B1 | 5/2005 | Koike et al. | |
| 2005/0255242 A1* | 11/2005 | Hass | C23C 14/04 427/248.1 |
| 2006/0150714 A1* | 7/2006 | Imhof | A61B 5/4266 73/29.01 |
| 2006/0208191 A1 | 9/2006 | Kessler et al. | |
| 2008/0144899 A1* | 6/2008 | Varma | G06K 9/522 382/129 |
| 2008/0170136 A1* | 7/2008 | Raynor | H04N 5/357 348/241 |
| 2009/0095616 A1* | 4/2009 | Lu | G01J 3/443 204/192.1 |

OTHER PUBLICATIONS

Granier, A., "Vapour flux density and transpiration rate comparisons in a stand of Maritime pine (Pinus pinaster Ait.) in Les Landes forest". Agricultural and Forest Meteorology, 51 (1990) 309-319.*
Baldocchi, Dennis, et al., "FluxNet: A new tool to study the temporal and spatial variability of ecosystem-scale carbon dioxide, water vapor, and energy flux densities". Bulletin of the American Meteorological Society, vol. 82, No. 11, Nov. 2001, 2415-2434.*
Berg, E.P., et al., "AquaFlux—A new instrument for water vapour flux density measurement". 4th International Symposium on Humidity & Moisture, Taipei, Sep. 2002, pp. 1-8.*
Webb, E.K., et al., "Correction of flux measurements for density effects due to heat and water vapour transfer". Quart. J. R. Met. Soc. (1980), 106, pp. 85-100.*

* cited by examiner

*Primary Examiner* — Bret Chen
(74) *Attorney, Agent, or Firm* — Blank Rome LLP

(57) ABSTRACT

A method of measuring vapor flux density including directing a light beam through a vapor flux to a pixel array sensor and using the pixel array sensor to measure attenuation of the light beam.

21 Claims, 11 Drawing Sheets

METHOD OF MEASURING VAPOR FLUX DENSITY

CLAIM OF PRIORITY

This application is a divisional of U.S. application Ser. No. 12/981,759, now U.S. Pat. No. 8,646,408, filed Dec. 20, 2010, which claims the benefit of U.S. Application No. 61/291,752, filed Dec. 31, 2009, the entire disclosures of which are incorporated herein by reference.

TECHNICAL FIELD

This invention relates to a deposition monitoring process, which can include a vapor flux monitor.

BACKGROUND

A photovoltaic device can be manufactured by forming one or more layers of material adjacent to substrate. The materials can include semiconductor materials or metals, for example. Layers can be formed by suitable deposition methods. Past manufacturing processes have been lacking in that they do not include effective means for measuring vapor flux properties of materials being deposited.

DETAILED DESCRIPTION

Figure 1:
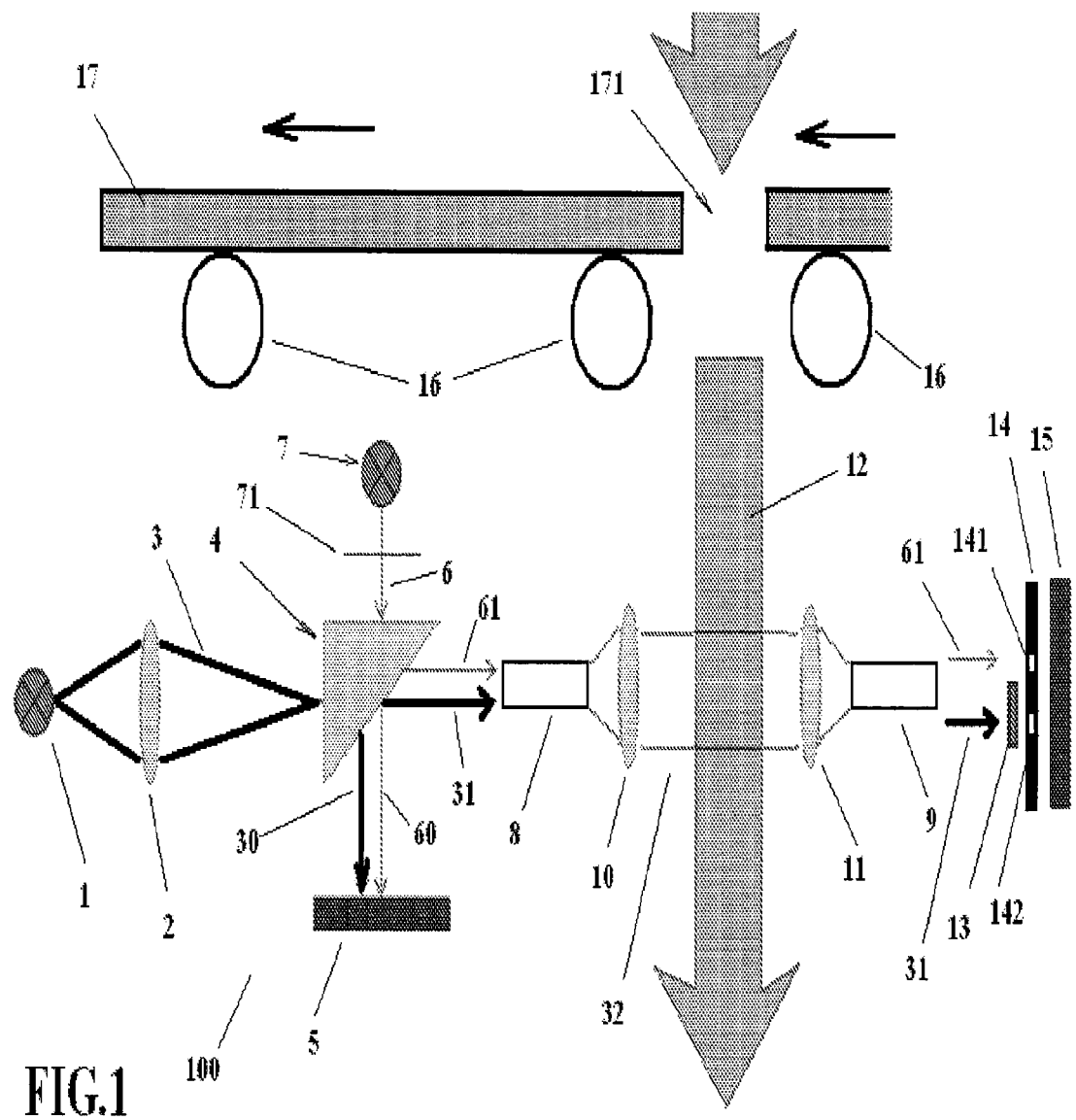
FIG. 1 illustrates a configuration of an in-situ flux monitor for in-line deposition process.

Photovoltaic devices can include multiple layers formed on a substrate. For example, a photovoltaic device can include layers of semiconductor, metal, and/or other suitable materials created (e.g., formed or deposited) adjacent to a substrate. Each layer may include more than one layer or film. Each layer can cover all or a portion of the device and/or all or a portion of the layer or substrate underlying the layer. For example, a "layer" can mean any amount of any material that contacts all or a portion of a surface. The process can be monitored in one aspect by observing and/or measuring information relating to the flux of the vapor being deposited, such as the vapor flux density. The flux can include vapor including atoms or other particles of a material being deposited on a surface of a substrate. For example, if vaporized material is being deposited in an in-line deposition process on the top surfaces of a plurality of in-line substrates, vapor that does not contact a substrate surface can flow as vapor flux through gaps between substrates to beneath the substrates. Information relating to vapor flux can be measured. For example, the density of the vapor flux, or vapor flux density (e.g., in terms of number of atoms or particles per unit volume of space) can be measured. Vapor flux density can be measuring using atomic absorption.

When a beam of light passes through a cloud of atoms (e.g., vapor flux) with a given density across the light beam diameter, photons at the characteristic wavelength can be absorbed by particular atoms. The amount of absorption depends on the number of particular atoms in the light path. Therefore, atomic absorption can be used to monitor the metal vapor flux. When an excited atom de-excites, it emits a photon of characteristic wavelength. Atomic absorption (AA) is the reverse of this process. When a beam of light at the characteristic wavelength passes through a cloud of atoms with certain density across the light beam diameter, photons are absorbed by the atoms. The amount of absorption depends on the number of atoms in the light path. Therefore, atomic absorption can be used to monitor the vapor flux of metal evaporation, chemical vapor deposition (CVD), or other vapor transition deposition process.

To measure the position-sensitive vapor flux density and deposition rate, a spatially dependent sensor of compact dimensions is developed with an in-situ flux monitor configuration for in-line deposition processes. By splitting and directing the measuring light beam through the vapor flux at different locations, position-sensitive flux information can be obtained. A pixel array sensor is used to measure the absorptions of the split measuring light beam. The pixel array sensor can be a 1D detector array (e.g. a line of photodiodes or an integrated line sensor) for a position-sensitive detection. The pixel array sensor can be a 2D detector array. A calibration light can be used. Correlating the absorptions to the flux density from calibration, the position-sensitive flux information can be extracted. Spectroscopy can also be used in conjunction with the vapor flux density measurement system.

In one aspect, a method of measuring position-sensitive vapor flux density can include directing a measuring light beam through a vapor flux of deposition to a pixel array sensor. The measuring light beam can include a wavelength capable of being absorbed by the vapor flux of deposition. The measuring light beam can be generated by a light source. The method can include measuring attenuation of the measuring light beam by the pixel array sensor. The method can include determining vapor flux density by calculating the absorption from the attenuation of the measuring light beam and correlating the absorption to vapor flux density.

The method can further include splitting the measuring light beam. The split portions of the measuring light beam can be directed through the vapor flux at different positions and detected by different segments of the pixel array sensor respectively. The method can include correlating the absorption to vapor flux density at different positions to obtain position-sensitive vapor flux density.

The method can further include generating a calibration light beam. The calibration light beam can be split and directed along the same measuring channel and through the vapor flux, and its attenuation can be detected by the same pixel array sensor. The method can include splitting the calibration light and the measuring light by a pixel array sensor mask including a top slit and bottom slit. One of the slits can be used for the calibration light, and the other one of the slits can be used for the measuring light, shuttering the calibration light beam during measurement. The method can include reading the pixel array sensor, subtracting a contribution from optical coating via the calibration light beam in the measuring channel and correlating absorption to vapor flux density after calibration.

The calibration light beam can be white light. The calibration light beam can be generated by a monochromatic light source. The calibration light can be designed to be absorbed by undesired optical coating, not the vapor flux. The pixel array sensor can include a charge-coupled device (CCD) detector. The pixel array sensor can include a complementary metal-oxide-semiconductor (CMOS) detector. The pixel array sensor can have a wavelength measurement range of about 100 to about 2000 nm, or about 100 to about 1000 nm, or about 200 to about 500 nm.

The method can further include directing a reference light beam to a second sensor without passing through the vapor flux. The reference light beam and the measuring light beam can be generated by the same light source. The method can include measuring attenuation of the reference light beam by the second sensor. The method can include calculating vapor flux density by comparing the attenuation of the measuring light beam and the attenuation of the reference light beam to eliminate the effect of fluctuation of the light source.

The measuring light beam and the reference light beam can be generated by a light source including a hollow cathode lamp. The measuring light beam and the reference light beam can be generated by a light source including a monochromatic light source.

In one aspect, a method to build an in-situ position-sensitive flux monitor system for in-line deposition process with plurality of separate rollers and plurality of moving substrates can include directing a measuring light beam along a measuring channel through a vapor flux of deposition to a pixel array sensor. The measuring light beam can include a wavelength capable of being absorbed by the vapor flux of deposition. The method can include directing a reference light beam to a second sensor without passing through the vapor flux. The method can include positioning the measuring channel under plurality of separate rollers and plurality of moving substrates. The method can include using the gap between the rollers to pass flux to the measuring channel. The method can include mounting the entire system on a backbone made from material with a substantially small coefficient of thermal expansion to minimize the possible misalignment due to thermal expansion. The method can include measuring attenuation of the measuring light beam by the pixel array sensor, measuring attenuation of the reference light beam by the second sensor. The method can include using the moving substrates and rollers as the flux and radiation shields for the pixel array sensor and second sensor. The method can include calculating vapor flux density by comparing the attenuation of the measuring light beam and the attenuation of the reference light beam to eliminate the effect of fluctuation of the light source, calculating the absorption from the attenuation, and correlating the absorption to vapor flux density.

The method can further include splitting the measuring light beam. The split portions of the measuring light beam can be directed through the vapor flux at different positions and detected by different segments of the pixel array sensor respectively. The method can include correlating the absorption to vapor flux density at different positions to obtain position-sensitive vapor flux density. The method can further include generating a calibration light beam. The calibration light beam can be split and directed along the same measuring channel and through the vapor flux, and its attenuation can be detected by the same pixel array sensor. The method can include splitting the calibration light and the measuring light by a pixel array sensor mask comprising a top slit and bottom slit. One of the slits can be used for the calibration light. The other one of the slits can be used for the measuring light. The method can include using the moving substrates to shutter the flux on and off. The method can include using the shutter-off position to calibrate the measurement. The method can include reading the pixel array sensor, subtracting a contribution from an undesired optical coating via the calibration light beam in the measuring channel, and correlating absorption to vapor flux density after calibration.

The method can further include positioning an additional flux and radiation shield to protect the pixel array sensor and second sensor. The shield can include a window transparent in the measuring wavelength range in the measuring channel. The method can include opening an aperture on the additional flux and radiation shield to allow the vapor flux to pass the measuring channel. The dimension of the aperture can be significantly bigger than the measuring light beam diameter. The pixel array sensor can include a charge-coupled device (CCD) detector. The pixel array sensor can include a complementary metal-oxide-semiconductor (CMOS) detector. The pixel array sensor can have a wavelength measurement range of about 100 to about 2000 nm, or about 100 to about 1000 nm, or about 200 to about 500 nm.

The measuring light beam and the reference light beam can be generated by a light source including a hollow cathode lamp. The measuring light beam and the reference light beam can be generated by a light source including a monochromatic light source. The mounting backbone can include a ceramic material. The mounting backbone can include graphite. The calibration light beam can be generated by a light source including a monochromatic light source.

A method of manufacturing an in-situ flux monitor system for in-line deposition process using a plurality of separate rollers and plurality of moving substrates can include generating a measuring light beam including a wavelength that can be absorbed by a vapor flux of deposition. The method can include creating a reference signal by splitting a portion of the measuring light beam. The portion of the light beam, the reference light beam, is directed along a reference channel without passing through the vapor flux. The method can include positioning the measuring channel under plurality of separate rollers and plurality of moving substrates. The method can include the substrates being transported on the rollers. The method can include passing flux through the gap between the rollers to the measuring channel. The method can include mounting the entire system on a backbone made from material with a very small coefficient of thermal expansion to minimize the possible misalignment due to thermal expansion. The method can include measuring the attenuation of the measuring light beam by a first sensor. The method can include measuring the attenuation of the reference light beam by a second sensor. The method can include calculating vapor flux density by comparing the attenuation of the measuring light beam and the attenuation of the reference light beam to eliminate the effect of fluctuation of the light source, calculating the absorption from the attenuation, and correlating the absorption to vapor flux density.

The method can further include generating a calibration light beam. The calibration light beam can be directed along the same measuring channel and through the vapor flux. The attenuation of the light beam can be detected by the same first sensor. The method can include splitting the calibration light and the measuring light by a first sensor mask comprising a top slit and bottom slit. One of the slits can be used for the calibration light. The other one of the slits can be used for the measuring light. The method can include using the moving substrates to shutter the flux on and off. The method can include using the shutter-off position to calibrate the measurement. The method can include reading the first sensor, subtracting the contribution from optical coating via the calibration light beam in the measuring channel, and correlating absorption to vapor flux density from calibration.

The method can further include positioning an additional flux and radiation shield to protect the first sensor and second sensor. The shield can include a window transparent in the measuring wavelength range in the measuring channel. The method can include opening an aperture on the additional flux and radiation shield to allow the vapor flux to pass the measuring channel. The dimension of the aperture can be significantly bigger than the measuring light beam diameter. The measuring light beam and the reference light beam can be generated by a light source including a hollow cathode lamp or monochromatic light to source. The mounting backbone can include ceramics or graphite. The calibration light beam can be generated by a monochromatic light source. The method can further include using the signal change caused by the moving substrates to count the number of substrates, check distances between the substrates, and compute the moving speed of substrates. The moving substrates shutter the flux on and off and the spacing between the moving substrates determines the length of signal change cycle.

In one aspect, an in-situ flux monitor system for in-line deposition process with plurality of separate rollers and plurality of moving substrates can include a first light source to generate a measuring light beam including a wavelength that can be absorbed by a vapor flux of deposition along a measuring channel. The system can include an optic device to create a reference signal by splitting a portion of the measuring light beam. The portion of the light beam, the reference light beam, can be directed along a reference channel without passing through the vapor flux. The system can include a plurality of optic fibers to direct the measuring channel under a plurality of separate rollers and plurality of moving substrates, which can be transported on the rollers. The flux can pass through the gap between the rollers to the measuring channel. The system can include a mounting backbone. The entire system can be mounted on the backbone and the backbone can be made from material with a substantially small coefficient of thermal expansion to minimize the possible misalignment due to thermal expansion. For example, the backbone can be made from a material having a smaller coefficient of thermal friction than a metal. The system can include a first sensor to measure the attenuation of the measuring light beam and a second sensor to measure the attenuation of the reference light beam. The system can include a measurement module to calculate vapor flux density by comparing the attenuation of the measuring light beam and the attenuation of the reference light beam to eliminate the effect of fluctuation of the light source, calculating the absorption from the attenuation, and correlating the absorption to vapor flux density.

The system can include a second light source to generate a calibration light beam. The calibration light beam can be directed along the same measuring channel and through the vapor flux, and its attenuation can be detected by the same first sensor. The system can include a first sensor mask comprising a top slit and bottom slit to split the calibration light and the measuring light. One of the slits can be used for the calibration light. The other one of the slits can be used for the measuring light. The system can include a configuration to use the moving substrates to shutter the flux on and off. The shutter-off position can be used to calibrate the measurement. The system can include a calibration module to read the first sensor, subtract the contribution from optical coating via the calibration light beam in the measuring channel, and correlate absorption to vapor flux density from calibration. The configuration can include an additional flux and radiation shield to protect the first sensor and second sensor. The shield can include a window transparent in the measuring wavelength range in the measuring channel. The system can include an aperture on the additional flux and radiation shield to allow the vapor flux to pass the measuring channel. The dimension of the aperture can be significantly bigger than the measuring light beam diameter. The first light source can include a hollow cathode lamp. The first light source can include a monochromatic light source. The mounting backbone can include ceramics. The mounting backbone can include graphite. The second light source can include a monochromatic light source.

The measurement module can further use the signal change caused by the moving substrates to count the number of substrates, check distances between the substrates, and compute the moving speed of substrates. The moving substrates can shutter the flux on and off. The spacing between the moving substrates can determine the length of signal change cycle. The optic fiber can include sapphire. The optic fiber can include quartz.

As described above, when a beam of light at the characteristic wavelength passes through a cloud of atoms with a given density across the light beam diameter, photons are absorbed by the atoms. The amount of absorption depends on the number of atoms in the light path.

For example, let
$I_{in}$=incident light intensity
$I_{out}$=transmitted light intensity
N=number of atoms the beam interacts.
Beer's law states that $$I_{out}=I_{in}\exp(-N/\alpha)$$

$\alpha$ is a constant that is related to the cross-section of optical absorption.

$$N=\alpha \ln(I_{in}/I_{out}).$$

The ratio $I_{out}/I_{in}$ is directly related N. Therefore AA can be used as a monitor of metal flux. Note that $$dI_{out}/dN=-(I_{out}/\alpha).$$

AA is most sensitive when $I_{out}$ is large, or when N is small. The major characteristic absorption lines of Cu, In, Zn, Mn, Fe, and Ga are shown below:

| | |
|---|---|
| Copper | 324.75(s)/327.40/217.90 nm |
| Gallium | 287.4/294.36(s)/403.3 nm |
| Zinc | 213.9(s) nm |
| Manganese | 279.5(s) nm |
| Indium | 303.94(s)/325.61 nm |
| Iron | 248.3(s) nm |

The notation 's' means the strongest. Therefore, the working wavelength of the light source can be in the range of some major characteristic absorption lines of the interested elements. For example, the working wavelength of the light source can be in the 200-350 nm range in the UV.

Referring to FIG. 1, position-sensitive flux monitor system 100 can be placed inside the deposition chamber under moving substrates 17 and rollers 16. Moving substrates 17 can be used to shutter vapor flux 12 off during the measurement.

Both moving substrates 17 and rollers 16 can be used to shield position-sensitive flux monitor system 100 from the vapor and radiation. Light source 1 can generate light beam 3 including a wavelength that can be absorbed by vapor flux 12. Light source 1 can include any suitable light source. In certain circumstances, light source 1 for AA can include a hollow cathode lamp (HCL) where an Ar or Ne plasma excites the atoms of interest to emit the characteristic lines. Light source 1 for AA can include a tunable laser, such as a tunable diode laser (TDL). Light source 1 can include a light emitting diode (LED). Light source 1 can emit light beam 3 having any suitable wavelength or range of wavelengths.

The intensity ratio $I_{out}/I_{in}$ can be used for the measurement. $I_{in}$ can be measured by shuttering off the metal vapor. Another detector can be used to monitor the HCL output. Therefore, corrections can be made to the light intensity if necessary. The transmission of the optical system may change due to metal deposition on the optical elements. If the metal vapor can be shuttered off to measure $I_{in}$, it is equivalent to an intensity change of the light source and be used as above. A white light source 7 (e.g., a light source that is not absorbed or scattered by the metal vapor) can also be used to monitor a change in the transmission.

Referring to FIG. 1, light beam 3 can be split into reference beam 30 and measuring beam 31 by splitter 4. Reference beam 30 can be detected by second sensor 5. White light source 7 can generate white light beam 6. Shutter 71 can be used to shutter white light beam 6. White light beam 6 can be split into reference beam 60 and calibration beam 61 by splitter 4. Optic fiber bundle 8 can be used to transmit measuring beam 31 and calibration beam 61. Measuring beam 31 and calibration beam 61 can be directed through vapor flux 12 in measuring channel 32. Measuring beam 31 and calibration beam 61 can be transmitted by optic fiber bundle 9 at the other side of vapor flux 12. Mask 14 having top slit 141 and bottom slit 142 can be used to split measuring beam 31 and calibration beam 61. The emission from the light source (e.g., an HCL) can include other background emission lines. A bandpass filter either at the source or at the detector can be used to filter the unwanted emission lines. For example, monochromatic filter 13 can be used to filter measuring beam 31. Any other suitable device can be used, for example, a spectrometer.

Pixel array sensor 15 can be a 2D sensor and can be used to measure the attenuation of measuring beam 31 and calibration beam 61. Lenses 2, 10, and 11 can be used for directing and coupling of light beam. In other circumstances, the location for sensing the metal flux can be positioned directly at the plume exciting the source. The width of the plume can be about 10-20 cm, for example, at exit of the source and can expand to about 80-120 cm. For example, the distance between the source exit to the plate can be about 50-70 cm. In some embodiments, in order not to interrupt the plume, the separation between the AA light probe and the detector path can be at least about 5-50 cm, for example, 10-20 cm. For example, the proximity to the exit of the source means components may be subjected to considerable radiation heating. Deposition of scattered metal atoms on the optics may also occur. Therefore, a shield (50 in FIG. 5) can be included in the design. All of these optic components can be positioned outside the deposition chamber on the atmospheric side. Light can be coupled into and out of the chamber. Pixel array sensor 15 can use a first dimension to detect position information and a second dimension to detect the spectral information using, for example, a spectrometer. A spectrometer can be used to monitor the characteristics of the light, or any other characteristic including the identity of the vapor material. The spectrometer can be positioned and utilized in any manner suitable to take spectroscopic measurements.

The pixel array sensor can have a wavelength measurement range from about 100 to about 2000 nm. The pixel array sensor can have a wavelength measurement range from about 100 to about 1700 nm. The pixel array sensor can have a wavelength measurement range from about 100 to about 1000 nm. The pixel array sensor can have a wavelength measurement range from about 200 to about 500 nm.

Figure 2:
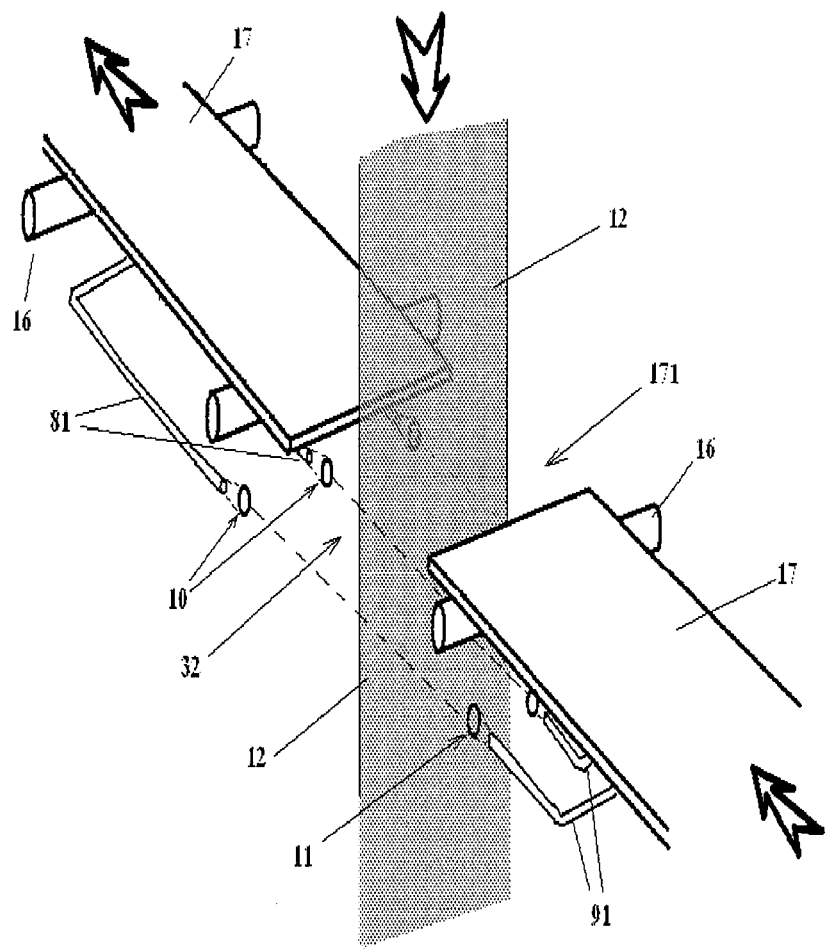
FIG. 2 is a perspective view illustrating a measuring light beam split by a plurality of fibers, directed through a vapor flux at different positions, and coupled on the other side of the vapor flux for calibration and measurement.
Figure 3:
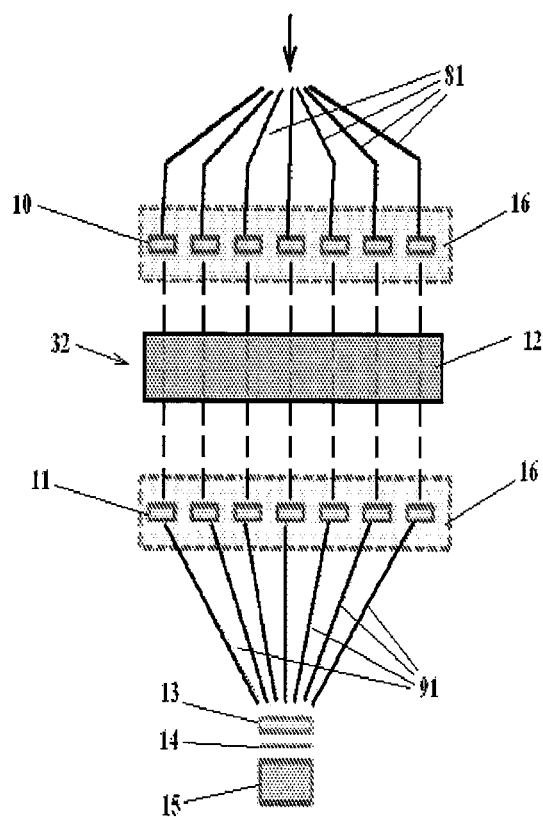
FIG. 3 is a top view illustrating the measuring light beam split by a plurality of fibers directed through a vapor flux at different positions, coupled on the other side of the vapor flux, and detected by a pixel array sensor.

Referring to FIGS. 2 and 3, measuring light beam 31 is split by plurality of optic fiber cables 81, directed through vapor flux 12 at different positions, and coupled on the other side of vapor flux 12. Since gap 171 between moving substrates 17 can be used to pass vapor flux 12 to measuring channel 32, position-sensitive flux density information can be obtained. Moving substrates 17 can be used as a shutter of vapor flux 12. Therefore, the signal can be used to sense the presence of a substrate and the time stamped information can allow the measurement of the translation speed of the substrates on rollers 16 as well as substrate counting. Each split portion of measuring beam 31 and calibration beam 61 is transmitted by plurality of optic fiber cables 91 at the other side of vapor flux 12 and illuminates a given segment of pixel array sensor 15. By measuring the attenuation of reference light beam 30 by second sensor 5 (FIG. 1), position-sensitive vapor flux density can be extracted by comparing the attenuation of each portion of the measuring light beam 31 and reference light beam 30 (FIG. 1), calculating the absorption from the attenuation by applying Beer's law, and correlating the absorption to vapor density at different positions in the flux. The optic fibers can include sapphire, quartz, or any other suitable optically transparent materials. The system can be used to calculate and/or measure any suitable characteristic based on the absorption, including the density of the vapor (e.g., the density of the vapor flux present in measuring light beam 31). The system can calculate and/or measure position-specific vapor and flux data in one or more dimensions and at various times for comparison.

Figure 4:
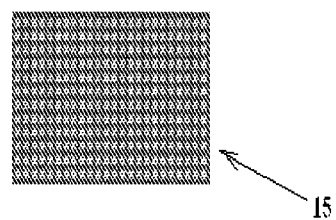
FIG. 4 is a close-in view of a pixel array sensor, a mask, and a monochromatic filter.
Figure 4:
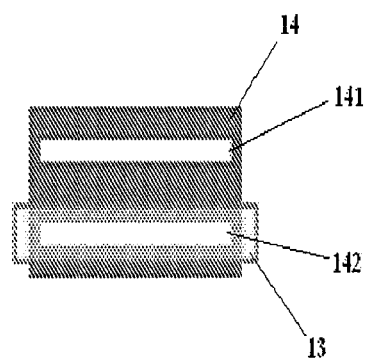

Referring to FIG. 4, mask 14 can include top slit 141 and bottom slit 142. Mask 14 can be positioned in front of pixel array sensor 15 to split measuring beam 31 and calibration beam 61. Top slit 141 can be used for calibration beam 61. Bottom slit 142 can be used for measuring beam 31. Monochromatic filter 13 can be used to filter measuring beam 31.

Figure 5:
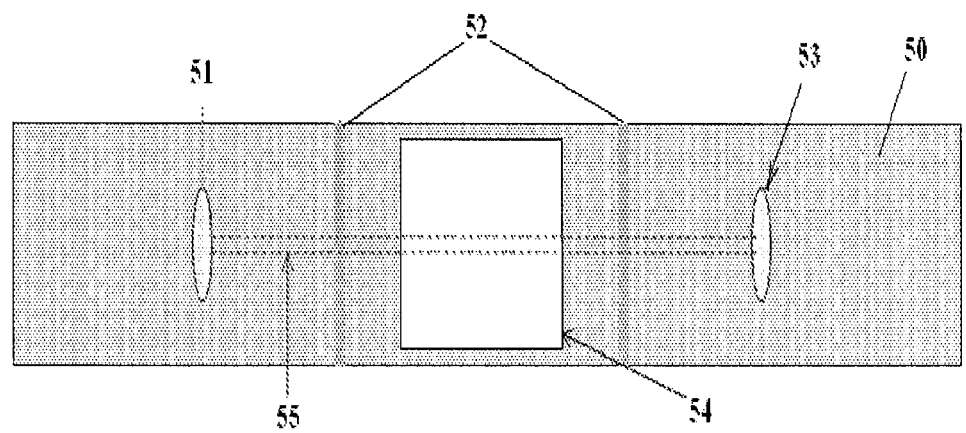
FIG. 5 is a top view of a shield with an aperture and windows transparent in the measurement wavelength.

Referring to FIG. 5, shield 50 can be included to address the protection of position-sensitive flux monitor system 100 (FIG. 1). All of these optic components can be positioned outside the deposition chamber on the atmospheric side. Light can be coupled into and out of the chamber through window 52 on the side walls of shield 50. Aperture 54 can be included on the top of shield 50 to allow flux to pass to measuring channel 32 (FIGS. 1 and 2). For example, aperture 54 can be a hole through which the flux can pass. To avoid impacts from material build-up on aperture 54 (shrinking of dimensions), optical beam diameter 55 can be significantly smaller than the opening of aperture 54. Windows 52 transparent in the measurement wavelength can be placed in measuring channel 32 between coupling lens 51 and 53 for protection. The diameter of related light coupling pipe holding the lenses should be significantly larger than the beam diameter. Finally, to avoid misalignment due to thermal expansion, the entire assembly of position-sensitive flux monitor system 100 with an in-situ flux monitor configuration for in-line deposition process can be mounted to a backbone made from material with a very small coefficient of thermal expansion (CTE) (e.g., ceramics or graphite). In certain circumstances, a sampling hole can be made through the heat shields and the wall of the source. The wall of the source can be hotter than the melt and thus there may not be metal deposition there. However, condensation can happen on the cooler heat shields outside. The gas pressure (including Se) can be in the millitorr range, there may be scattering of the metal atoms off the line of sight and be deposited on the edge of the hole on the shield. The change in the sampling hole-size can change the sampling flux and periodic maintenance may be used to clean out the sampling hole.

Figure 6:
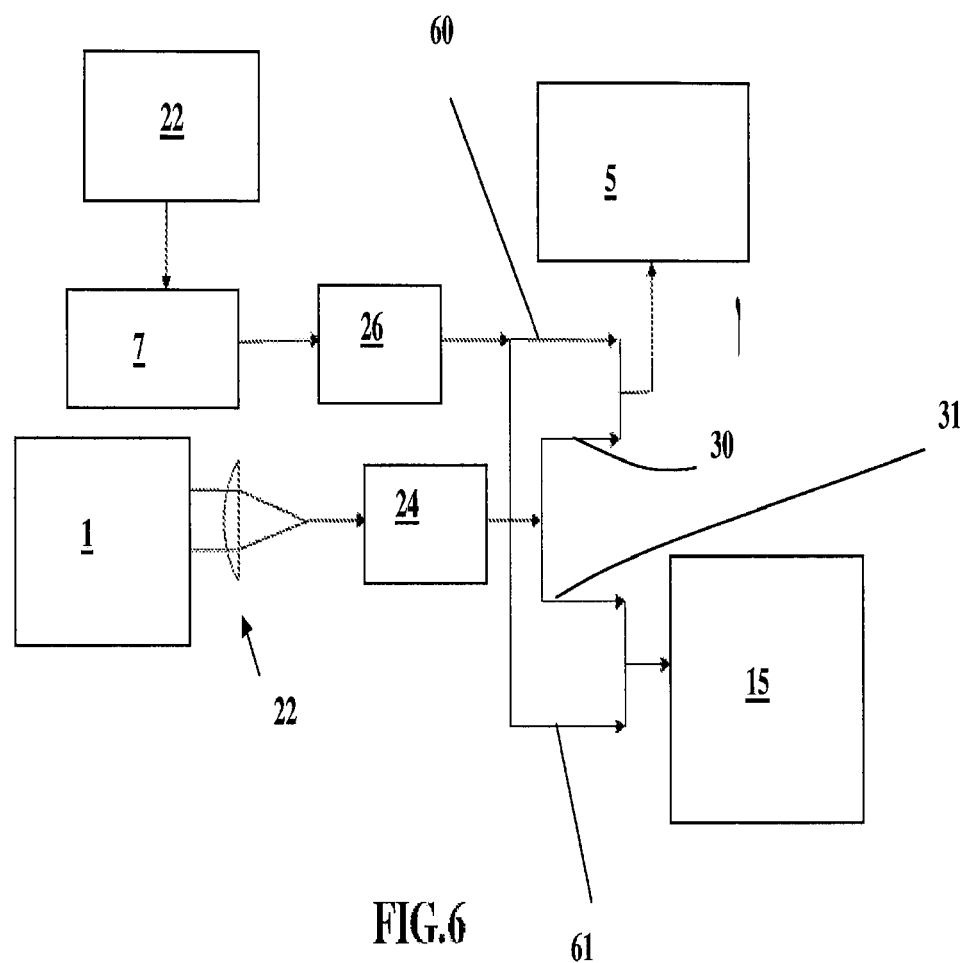
FIG. 6 illustrates a schematic setup of optical elements of the system.

Referring to FIG. 6, depicting a setup of optical elements of a flux monitor system, light source 1 (e.g., HCL) can remain on during the experiment to maintain stability. The light beam 3 from light source 1 is coupled through collimating lens 22 to optical fiber 24. The light can be split into reference beam 30 and measuring beam 31. A fiber optic attenuator 24 can be used to adjust the light intensity at any appropriate point. Measuring beam 31 is transmitted to pixel array sensor 15 and reference beam 30 is transmitted to second sensor 5, for example, as described above. White light source 7, (e.g., a white LED) can be turned on and off by any suitable control system, including, for example computer system 22 via, for example a shutter or attenuator. It can be split into also split into a reference beam 60 for monitoring at second sensor 5 and calibration beam 61 transmitted to pixel array sensor 15.

Figure 7:
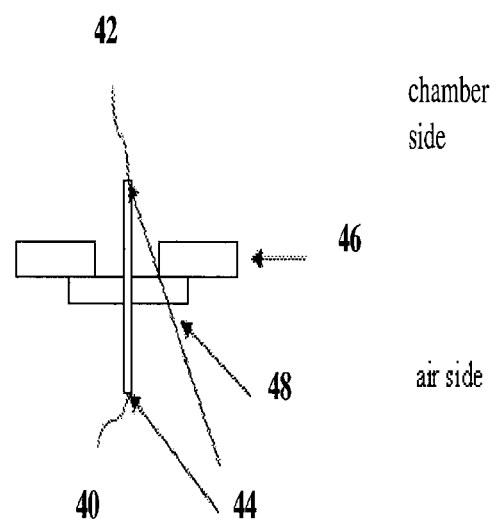
FIG. 7 illustrates a setup to couple the light through the chamber wall from the air side to the vacuum side.

Referring to FIG. 7, depicting a portion of the deposition chamber, the light (e.g., from a measuring beam 31 (FIG. 6)) can be coupled through the chamber wall 46 from the air side to the vacuum side. Because there may be a difference between the temperature on the vacuum side of the chamber (which may be, for example, about 250 degrees C.) and the chamber wall (which may be, for example, about 50 degrees C.), the choice of the vacuum feedthrough and the optical fiber can be selected to withstand these temperatures and/or difference between these temperatures. The feedthrough can occur through flange 48 adjacent to an opening in chamber wall 46. Optical fibers 40, 42 can be coupled across flange 46 using a suitable optical connector 44, such as an SMA 905 optical connector. There can be two such feedthroughs, one for guiding the light for AA into the chamber, and one for guiding the signal light out from the chamber.

In certain circumstances, the location for sensing the metal flux can be underneath the conveyor system with measurement occurring in the space in between plates. For example, there can be 2-4 cm in between the plates on the conveyor. The conveyor speed can be 10-100 cm/min. Therefore, there can be a 1-25 s gap at which the metal flux moves through the space between the conveyor rollers. The metal flux can be available for monitoring. The advantages are the following: there is little interference to the metal plume and the deposition process; the AA optics are not subjected to the radiation heat from the source, however, it may be shielded from the radiation heat from the heaters at the bottom of the chamber; in addition, the density of the plume is less. The signal might be smaller, but metal deposition on the optical and sensor components can be reduced, especially since the flux is shuttered by the plates a portion of the time (about 3 cm/61 cm, meaning about 5% transmission or about 95% blocked). When the metal flux is shuttered, a direct measure of $I_{in}$ can be obtained and there may not be a need for the monitoring of the light output from the HCL or using a white light source for correction to transmission. Another solution is to install a mechanical shutter. The introduction of the Se flux may change the shape of the plume and hence affect the flux monitored by AA even if the integrated flux for deposition remains the same. The effect from the Se can be studied experimentally in a separate test chamber.

Figure 8:
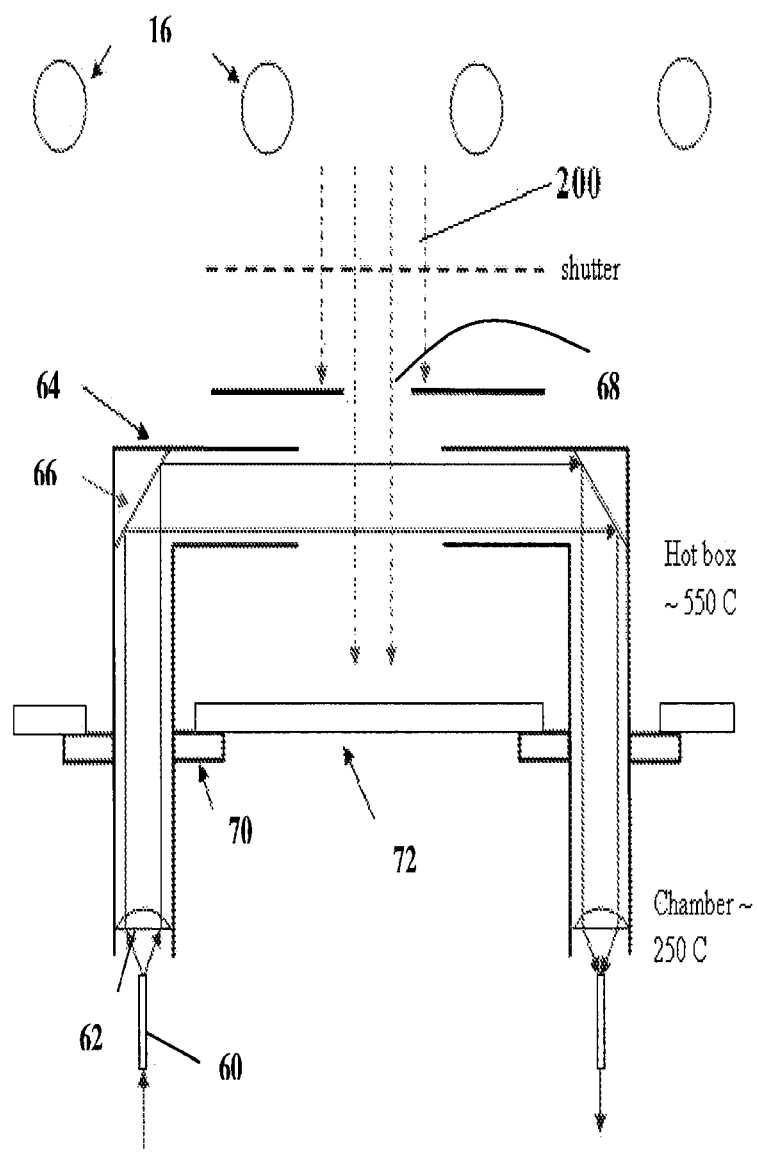
FIG. 8 illustrates a setup to couple the light in and out of the shield.

FIG. 8 depicts an in-situ vapor flux monitor system having components in a chamber and an inner chamber (e.g. "hot box") to form a functional feedthrough in the system. The light can be coupled in and out of the inner chamber, in which the temperature can be at 400-800 degrees C. The feedthrough can include one or more segments of conduit 64 or any other material suitable for transversing inner chamber flange 70 in inner chamber wall 72. A portion of the feedthrough can be mounted at the bottom of the inner chamber as the sampling location can be underneath conveyor rollers 16, as shown in FIG. 8. A light beam can be transmitted through optical fiber 60 and across inner chamber wall 72 via conduit 64. The light beam can pass through collimating lens 62 to convert the light from optical fiber 60 into a parallel beam outside the inner chamber, where the temperature can be 200-300 degrees C. The parallel beam can be transmitted into the feedthrough. Conduit 64 can include any suitable configuration, size, or material. For example, conduit 64 can include tubing. Conduit 64 can include stainless steel. Conduit 64 can include a material having a substantially small coefficient of thermal expansion (CTE).

Conduit 64 can be attached to inner chamber wall 72 by attaching it to flange 70, for example, by welding. Stainless steel can be selected as a material for use in conduit 64 because stainless steel has low thermal conductivity and is resistant to Se. The length and thickness of conduit 64 can be adjusted to bridge the temperature difference between the inside of the chamber (for example, about: 200-300 degrees C.) and the inside the inner chamber (for example, about 500-600 degrees C.). The light beam from optical fiber 60 can be transmitted through conduit 64 by reflecting it in the suitable direction, where there is a turn in conduit 64, for example. Reflector 66 can be used to reflect the light beam. Reflector 66 can include, for example, a stainless steel mirror or UV prism, or any other suitable reflector, situated at any suitable angle (e.g., 45 degrees to change the direction of the light beam by 90 degrees). Using a stainless steel mirror reduces complications that might result from possible metal deposition on the prism surfaces. The light beam can be directed toward vapor flux 200. As shown in FIG. 8, conduit 64 reduces the amount of deposition on reflector 66 from vapor flux 200.

When the light beam is directed at vapor flux 200, vapor flux information can be monitored as described above, for example, based on atomic absorption. An aperture or slit 68 can be used to control the amount of metal flux 200 sampled. This is in the case where the absorption is too high that the AA signal is not sensitive enough to the changes in the metal flux. A mechanical shutter can be included to eliminate the necessity of a white light path even in the case that the system does not have a plate in the chamber to be used as a shutter. After passing through vapor flux 200, the light beam can be transmitted back outside inner chamber wall 72 through an additional length of conduit, including any suitable reflectors to direct the light beam outside the inner chamber.

Figure 9:
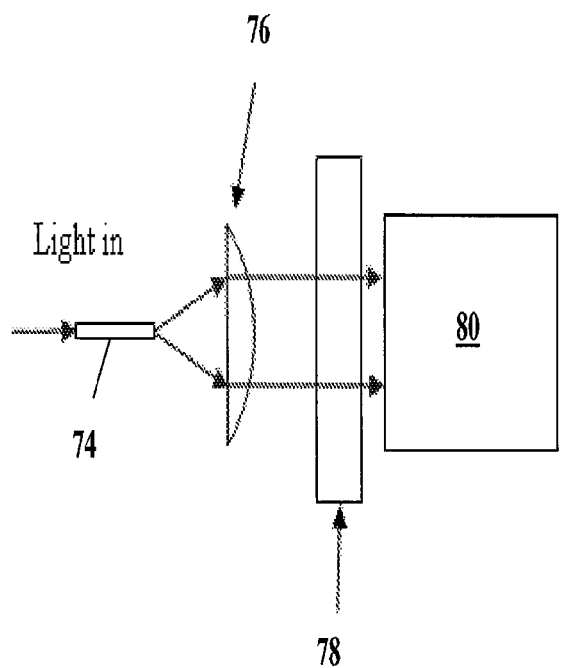
FIG. 9 is a perspective view illustrating that a UV bandpass filter can be positioned in front of the detector.

With shuttering capability, both $I_{in}$ and $I_{out}$ can be obtained with a single detector in some embodiments. As mentioned above, the HCL has a background besides the main emission line. Referring to FIG. 9, light transmitted through optical fiber 74 can be collimated by passing it through collimating lens 76. The collimated light beam can then be to passed through a UV bandpass filter 78 and to detector 80, which can include a silicon photodiode, which can be positioned outside the deposition chamber.

In one embodiment, a procedure for metal flux measurement includes the following steps:
1. Set HCL optical attenuator to zero transmission. Read the background signal $I_{back}$. $I_{back}$ is from stray light and the dark current of the detector.
2. With shutter on (no metal flux), adjust the fiber optic attenuator so that the silicon photodiode output is within the linear range of the detector. The signal $I_{open}=I_{in}+I_{back}$.
3. Open the shutter (metal flux on). The signal is $I_{open}=I_{out}+I_{back}$.

From Beer's law:

$$N=\alpha \ln [(I_{shut}-I_{back})/(I_{open}-I_{back})].$$

Figure 10:
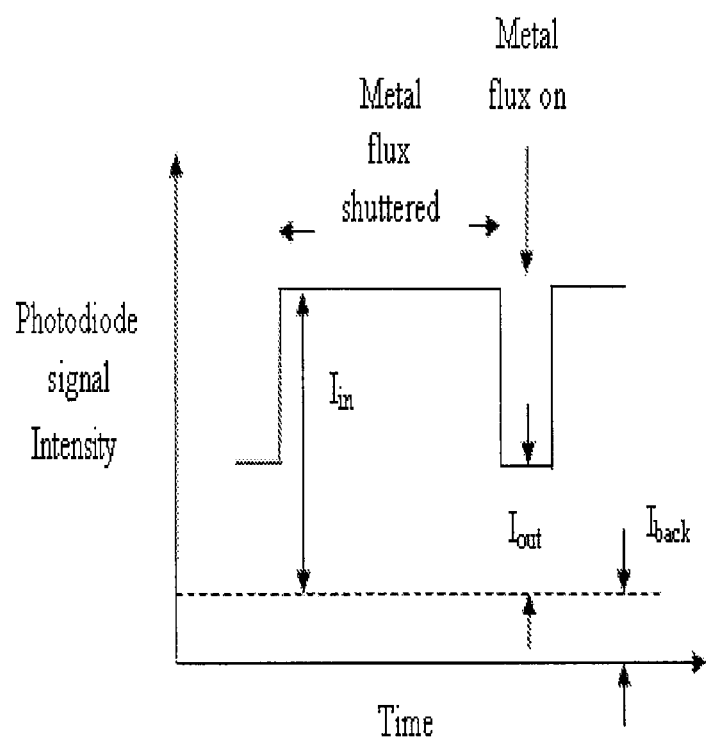
FIG. 10 is a diagram of a photodiode output waveform.
Figure 11:
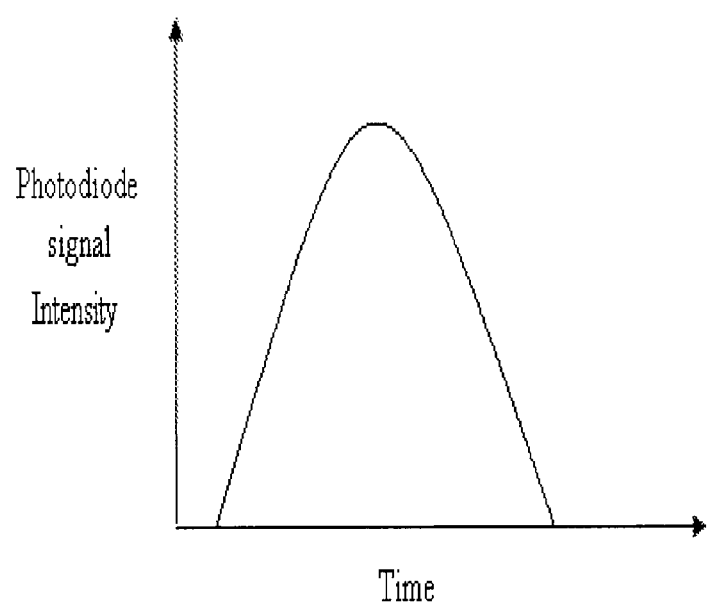
FIG. 11 is a diagram of a photodiode output waveform.

The value for α can be measured by directly measuring the thickness of the deposited film. Referring to FIG. 10, the photodiode output waveform is shown. During production, the moving plate can act as a shutter. As shown in FIG. 10, the photodiode output waveform can be idealistic square wave function in case of shuttered flux. In some embodiments, the waveform can have a sloped signal, as shown in FIG. 11. The signal can have any slope that can result from the flux, including in the case of a shuttered flux.

In the case when the metal flux cannot be shuttered, the light intensity monitoring photodiode and the "white" LED can be included to calibrate out any change in the transmission in the AA optical path e.g. due to metal deposition on the optical elements. The light intensity monitoring photodiode can be called PD2. The AA signal photodiode can be called PD1. The calibration can be made between PD1 and PD2 for both the AA sensing light and the white LED, assuming that the background signals from the two PDs are always subtracted already.

In certain circumstances, procedure for calibration can be:
1. Metal source off
2. Turn on HCL until stable
3. With white LED off or LED fiber attenuator set to zero output, set the HCL light level to a convenient value for measurement using the HCL fiber attenuator
4. Read PD1 and PD2 outputs
5. Initial calibration factor $k_{HCLi}$=PD1 output/PD2 output
6. Take out the UV bandpass filters for the photodiode detectors
7. With HCL fiber attenuator set to zero output, set the LED light level to a convenient value for measurement using the LED fiber attenuator
8. Read PD1 And PD2 outputs
9. Initial calibration factor $k_{LEDi}$=PD1 output/PD2 output In other circumstances, during metal flux measurement, the HCL can be kept on to maintain its stability. Therefore, PD1 can always have an output $I_{AA}$ as the AA signal. However, the transmission of the optics may change due to metal deposition on the optics elements. A correction measurement can be made. For this measurement, the white LED whose light is not attenuated to any significant extent by the metal flux can be used. The procedure to make transmission correction can be:
1. Block off the HCL light
2. Take out the UV bandpass filters
3. LED on
4. Take reading:
    a. PD1: $I_{LED1}$
    b. PD2: $I_{LED2}$
5. Take the ratio $k_{LED}=I_{LED1}/I_{LED2}$
6. Transmission correction factor $\beta=k_{LEDi}/k_{LED}$
7. The transmission correction factor has to be applied to the AA signal.
8. Turn off LED
9. Unblock HCL
10. Replace UV bandpass filters
11. Take reading:
    a. PD1: $I_{AA}$
    b. PD2: $I_{HCL}$ $$I_{out} = I_{AA}$$
$$I_{in} = I_{HCL} * k_{HCLi}/\beta.$$

Therefore $$N = \alpha \ln(I_{in}/I_{out})$$
$$= \alpha \ln(I_{HCL} * k_{HCLi}/\beta I_{AA})$$
$$= \alpha \ln[(PD2\ signal/PD1\ signal) * (k_{HCLi}/\beta)]$$

Here α has the same value as the α for the shuttered case.

A number of embodiments of the invention have been described. Nevertheless, it will be understood that various modifications may be made without departing from the spirit and scope of the invention. It should also be understood that the appended drawings are not necessarily to scale, presenting a somewhat simplified representation of various preferred features illustrative of the basic principles of the invention.

What is claimed is:

1. A method of measuring position-sensitive vapor flux density comprising:
   directing a measuring light beam through a vapor flux of deposition to a pixel array sensor, wherein the measuring light beam includes a wavelength capable of being absorbed by the vapor flux of deposition;
   measuring attenuation of the measuring light beam by the pixel array sensor;
   calculating the absorption from the attenuation of the measuring light beam; and
   calculating a vapor flux density by correlating the absorption to a vapor flux density.

2. The method of claim 1, wherein the method further comprises:
   splitting the measuring light beam, wherein the split portions of the measuring light beam are directed through the vapor flux at different positions and detected by different segments of the pixel array sensor respectively; and
   correlating the absorption to vapor flux density at different positions to obtain position-sensitive vapor flux density.

3. The method of claim 1, wherein the method further comprises:
   generating a calibration light beam, wherein the calibration light beam is split and directed along a same channel through the vapor flux as the measuring beam, and its attenuation is detected by the same pixel array sensor;
   splitting the calibration light and the measuring light by a pixel array sensor mask comprising a top slit and bottom slit, wherein one of the slits can be used for the calibration light, the other one of the slits can be used for the measuring light; shuttering the calibration light beam during measurement; and
   reading the pixel array sensor, subtracting a contribution from undesired optical coating via the calibration light beam in the measuring channel, and correlating absorption to vapor flux density after calibration.

4. The method of claim 3, wherein the calibration light beam is white light.

5. The method of claim 3, wherein the calibration light beam is generated by a monochromatic light source, wherein the calibration light can only be absorbed by optical coating, not the vapor flux.

6. The method of claim 1, wherein the pixel array sensor comprises a charge-coupled device detector.

7. The method of claim 1, wherein the pixel array sensor comprises a complementary metal-oxide-semiconductor detector.

8. The method of claim 1, wherein the pixel array sensor comprises a charge-coupled device detector having a wavelength measurement range of about 200 to about 500 nm.

9. The method of claim 1, wherein the pixel array sensor comprises a complementary metal-oxide-semiconductor detector having a wavelength measurement range of about 200 to about 500 nm.

10. The method of claim 1, wherein the pixel array sensor comprises a charge-coupled device detector having a wavelength measurement range of about 100 to about 2000 nm.

11. The method of claim 1, wherein the pixel array sensor comprises a complementary metal-oxide-semiconductor detector having a wavelength measurement range of about 100 to about 2000 nm.

12. The method of claim 1, wherein the method further comprises:
   directing a reference light beam to a second sensor without passing through the vapor flux, wherein the reference light beam and the measuring light beam are generated by the same light source;
   measuring attenuation of the reference light beam by the second sensor; and calculating vapor flux density by comparing the attenuation of the measuring light beam and the attenuation of the reference light beam to eliminate the effect of fluctuation of the light source.

13. The method of claim 12, wherein the measuring light beam and the reference light beam are generated by a light source comprising a hollow cathode lamp.

14. The method of claim 12, wherein the measuring light beam and the reference light beam are generated by a light source comprising a monochromatic light source.

15. A method measuring a vapor flux density in an in-line deposition process comprising:
   directing a measuring light beam along a measuring channel through a vapor flux of deposition to a pixel array sensor, wherein the measuring light beam includes a wavelength capable of being absorbed by the vapor flux of deposition and the measuring channel is under a plurality of separate rollers and a plurality of separate substrates;
   directing a reference light beam to a second sensor without passing through the vapor flux;
   using the gap between the rollers to pass flux to the measuring channel; measuring attenuation of the measuring light beam by the pixel array sensor;
   measuring attenuation of the reference light beam by the second sensor; using the moving substrates and rollers as the flux and radiation shields for the pixel array sensor and second sensor; and
   calculating vapor flux density by comparing the attenuation of the measuring light beam and the attenuation of the reference light beam to eliminate the effect of fluctuation of the light source, calculating the absorption from the attenuation, and correlating the absorption to vapor flux density.

16. The method of claim 15, wherein the method further comprises:
   splitting the measuring light beam, wherein the split portions of the measuring light beam are directed through the vapor flux at different positions and detected by different segments of the pixel array sensor respectively; and
   correlating the absorption to vapor flux density at different positions to obtain position-sensitive vapor flux density.

17. The method of claim 15, wherein the method further comprises:
   generating a calibration light beam, wherein the calibration light beam is split and directed along the same measuring channel and through the vapor flux, and its attenuation is detected by the same pixel array sensor;
   splitting the calibration light and the measuring light by a pixel array sensor mask comprising a top slit and bottom slit, wherein one of the slits can be used for the calibration light, the other one of the slits can be used for the measuring light; using the moving substrates to shutter the flux on and off;
   using the shutter-off position to calibrate the measurement; and
   reading the pixel array sensor, subtracting a contribution from optical coating via the calibration light beam in the measuring channel, and correlating absorption to vapor flux density after calibration.

18. The method of claim 17, wherein the calibration light beam is generated by a light source comprising a monochromatic light source.

19. The method of claim 15, wherein the method further comprises:
   positioning an additional flux and radiation shield to protect the pixel array sensor and second sensor, wherein the shield comprises a window transparent in the measuring wavelength range in the measuring channel; and
   opening an aperture on the additional flux and radiation shield to allow the vapor flux to pass the measuring channel, wherein the dimension of the aperture is significantly bigger than the measuring light beam diameter.

20. The method of claim 15, wherein the measuring light beam and the reference light beam are generated by a light source comprising a hollow cathode lamp.

21. The method of claim 15, wherein the measuring light beam and the reference light beam are generated by a monochromatic light source.

* * * * *